United States Patent [19]

Silvestrini

[11] Patent Number: 4,708,132

[45] Date of Patent: Nov. 24, 1987

[54] FIXATION DEVICE FOR A LIGAMENT OR TENDON PROSTHESIS

[75] Inventor: Thomas A. Silvestrini, East Lyme, Conn.

[73] Assignee: Pfizer-Hospital Products Group, Inc., New York, N.Y.

[21] Appl. No.: 821,948

[22] Filed: Jan. 24, 1986

[51] Int. Cl.⁴ .............................................. A61F 5/04
[52] U.S. Cl. .............................................. 128/92 YF
[58] Field of Search .......... 128/92 Y, 92 YW, 92 YF, 128/92 YE; 623/13, 2, 12, 1

[56] References Cited

U.S. PATENT DOCUMENTS

| | | | |
|---|---|---|---|
| 2,453,056 | 11/1948 | Zack | 128/334 C |
| 3,973,277 | 8/1976 | Semple | 128/92 YF |
| 4,246,660 | 1/1981 | Wevers | 128/92 YF |
| 4,484,570 | 11/1984 | Sutter | 128/92 YF |
| 4,585,458 | 4/1986 | Kurland | 623/13 |
| 4,610,688 | 9/1986 | Silvestrini | 623/12 |

FOREIGN PATENT DOCUMENTS 191081  8/1957  Austria ........................ 128/92 YF Primary Examiner—Gregory E. McNeill
Attorney, Agent, or Firm—Peter C. Richardson; Lawrence C. Akers; Elizabeth O. Slade

[57] ABSTRACT

A device for affixing a pretensioned ligament or tendon prosthesis to a bone of a patient includes a hollow elongated sleeve adapted to fit within a through drill hole in the bone and a cooperating wedge. A portion of the bore of the hollow sleeve is tapered with decreasing bore cross-sectional thickness towards the front end of the elongated sleeve. Th wedge is shaped so that a portion of a ligament or tendon prosthesis can be securely trapped between the wedge and the inner wall of the sleeve when the wedge is fully advanced forwardly within the sleeve. The device also includes a locking nut or ferrule for releasably locking the sleeve and wedge together with the wedge fully advanced within the sleeve, and a releasable bolt/washer assembly for preventing the prosthesis from being pulled forwardly through the drill hole in the patient's bone. The device is easy to use and provides a highly secure fixation of the pretensioned prosthesis.

18 Claims, 11 Drawing Figures

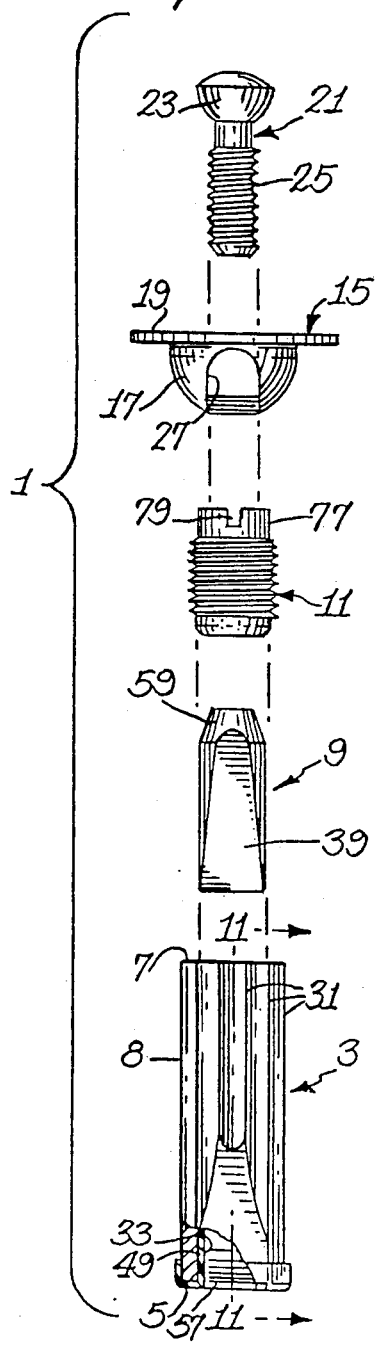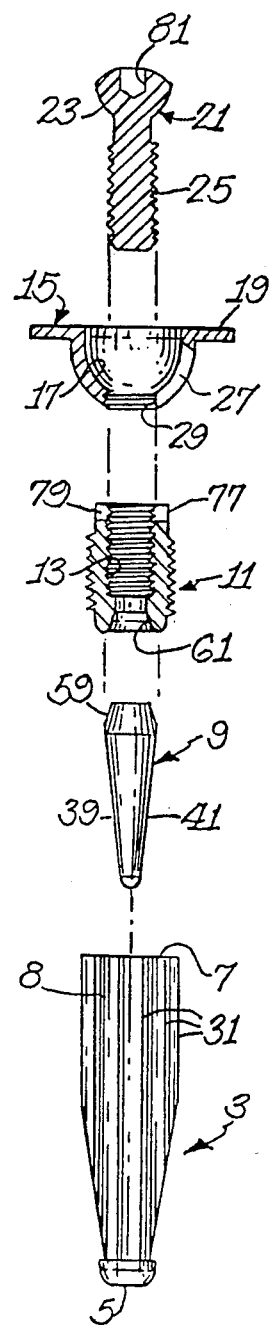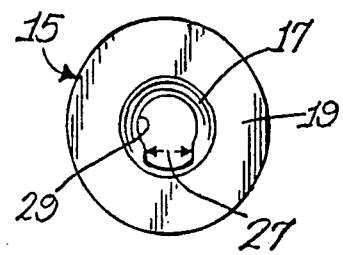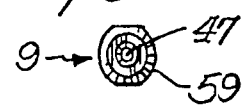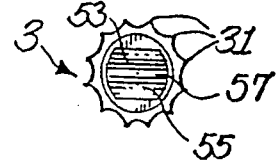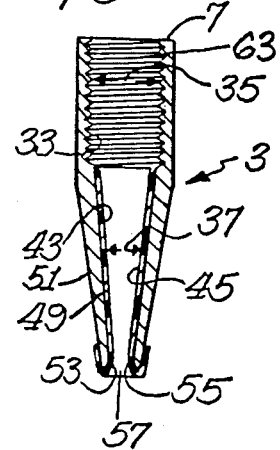

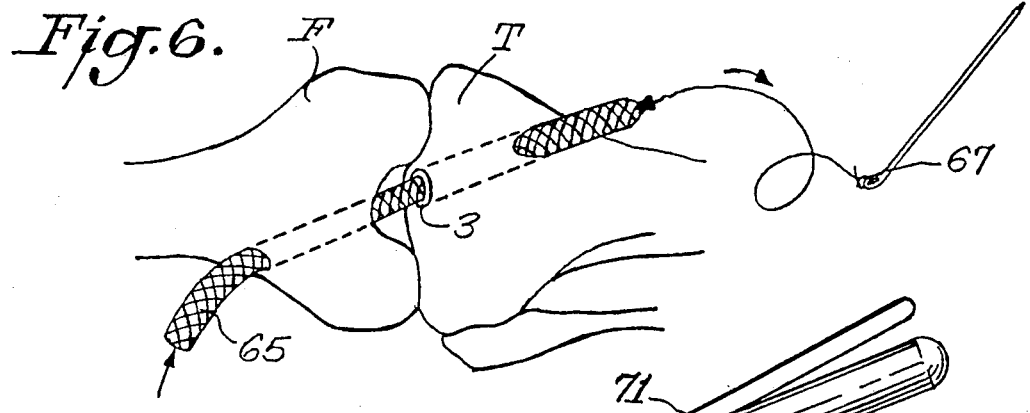
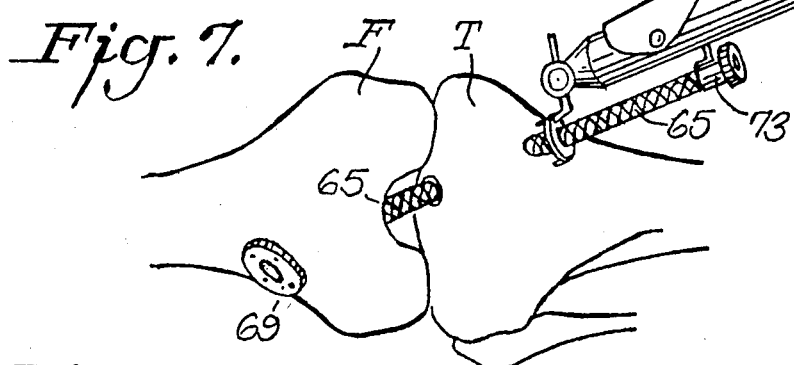
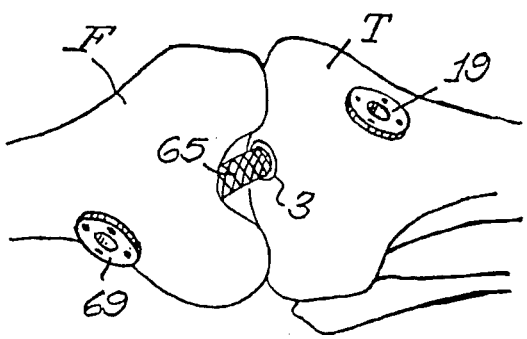
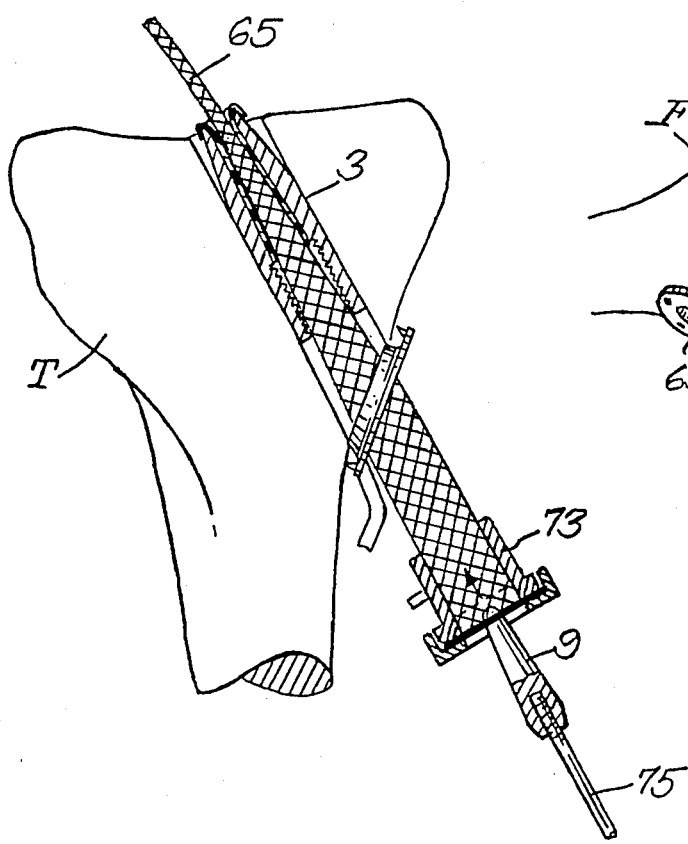

FIXATION DEVICE FOR A LIGAMENT OR TENDON PROSTHESIS

BACKGROUND OF THE INVENTION

A wide variety of elongated prostheses have been proposed for the repair or replacement of diseased or damaged ligaments and tendons. One particular example is the ligament or tendon prosthesis disclosed in copending, commonly assigned U.S. patent application Ser. No. 481,612, filed Apr. 4, 1982, entitled "Triaxially-braided Fabric Prosthesis". This prosthesis comprises an elongated triaxially-braided multicomponent fabric element (e.g. a braided tube), and has the capacity to approximate the mechanical behavior of various ligaments and tendons (depending on the particular selection of component fibers) while exhibiting an excellent fatigue resistance. This U.S. application Ser. No. 481,612 is incorporated herein by reference in its entirety.

One of the significant problems associated with the design of an artificial ligament or tendon prosthesis is the proper design of the means for fixation of the prosthesis to the patient's bone structure, typically with the prosthesis in a state of pretension. Such a fixation device should be securely held to the bone and should be capable of firmly gripping a portion of the prosthesis without damaging it. In particular, it is important that the prosthesis and fixation device not interact in use in such a way as to significantly detract from the inherent fatigue resistance of the active prosthesis structure itself, for example by excessive abrasive wear between the prosthesis and the fixation device.

SUMMARY OF THE INVENTION

It is therefore an object of the present invention to provide a device for the fixation of a pretensioned ligament or tendon prosthesis to a bone of a patient, in particular a tubular braided prosthesis, which is simple in construction and easy to use, is securely held to the patient's bone with the prosthesis in a pretensioned state, and which is capable of securely gripping the prosthesis without damaging it, which would significantly detract from the fatigue resistance of the prosthesis or otherwise adversely affect the performance of the prosthesis in vivo.

This and other objects of the invention are achieved with a novel fixation device comprising: a hollow elongated sleeve adapted to fit within a through drill hole in a patient's bone and having a front end, a rear end, an inner wall defining a bore and an outer wall, with the bore being open at both the front and rear ends of the sleeve and tapered over a portion of its length with decreasing cross-sectional bore thickness, in at least one dimension, towards said front end of the sleeve; a wedge capable of being inserted through the rear end of the sleeve and advanced forwardly into said tapered portion of the bore until coming to a position of abutment with the inner wall of the sleeve, with a pair of opposed faces on the outer surface of the wedge being, when the wedge is in said position of abutment, disposed within said tapered bore portion and substantially congruent with the adjacent surfaces of said inner wall; means for locking the sleeve and the wedge together in a rigid assembly with the wedge in said position of abutment; and means for holding said rigid assembly to said bone in such a manner that the assembly cannot be pulled forwardly through the drill hole in the patients' bone. In use, a portion of the prosthesis is securely trapped by friction between the wedge and the inner wall of the sleeve when the wedge is locked in the fully advanced position within the sleeve. The implantation of the fixation device and its connection to the prosthesis is a relatively simple matter because, among other things, the surgeon needs to insert the various elements of the fixation device only through the proximal end (as defined with respect to the surgeon) of the through drill hole in the patient's bone.

It is highly preferred that the adjacent surfaces of the wedge and the inner wall of the sleeve between which the prosthesis is held when the wedge is in the tapered portion of the bore both be made of a strong, resilient polymeric material to prevent damage to the prosthesis caused by compression thereof and to reduce any abrasive wear between the fixation device and the prosthesis. These factors are especially important when the prosthesis is comprised of braided polymeric fibers. Thus, both the sleeve and the wedge may be metallic parts lined with a polymeric material or, as one alternative, the wedge may be a part of one-piece polymeric construction.

It is also preferred that both the means for locking the sleeve and wedge together and the means for holding the sleeve/wedge assembly against forward pulling through the through drill hole by the pretensioned prosthesis be releasable, so that the readjustment, retensioning or replacement of a prosthesis, if necessary, can be accomplished using arthroscopic techniques without extensive surgery.

Thus, for example, the sleeve/wedge locking means may comprise an externally threaded locking nut or ferrule adapted to be screwed into an internally threaded portion of the sleeve (to the rear of the tapered bore portion) until it firmly presses the wedge forwardly against the inner wall of the sleeve. A releasable sleeve/wedge assembly holding means may comprise a washer adapted to lie against the cortical bone adjacent the rear end of the through drill hole, thereby acting to distribute prosthesis loads over a large surface area of cortical bone, and a bolt having a head adapted to engage the washer and a shank externally threaded over at least a portion of its length. The shank is adapted to be screwed into either an internally threaded axial bore provided in the locking nut or an internally threaded portion of the sleeve. Aside from its releasability, another important feature of this embodiment is that the length of the fixation device, i.e. the distance between the washer and the front end of the hollow sleeve, can be universally adjusted by the surgeon within wide limits during the implantation of the prosthesis to accommodate for anatomical variations from patient to patient.

Various other preferred features of the fixation device of the present invention are described below in the detailed description of the invention.

Finally, the present invention comprises a novel method for the fixation of a pretensioned ligament or tendon prosthesis involving the use of the novel fixation device of the invention.

DETAILED DESCRIPTION OF THE INVENTION

The invention will be described in detail with reference to a preferred embodiment thereof, which is a fixation device for a pretensioned anterior cruciate ligament (ACL) prosthesis. Reference to this embodiment does not limit the scope of the invention, which is limited only by the scope of the claims. In the drawings:

FIG. 1 is an exploded top plan view of a fixation device of the invention with a portion of the hollow elongated sleeve shown in section;

FIG. 2 is an exploded side view of the device of FIG. 1 with all components thereof shown in section except for the sleeve and wedge (which are shown in an elevational view);

FIG. 3 is a rear elevational view of the holding washer of the device of FIG. 1;

FIG. 4 is a rear elevational view of the wedge of the device of FIG. 1;

FIG. 5 is a rear elevational view of the sleeve of the device of FIG. 1;

FIGS. 6 to 10 illustrate various steps in the use of the device of FIG. 1 in the implantation of a pretensioned ACL prosthesis; and FIG. 11 is a sectional view taken along line 11—11 of FIG. 1.

Figure 9:
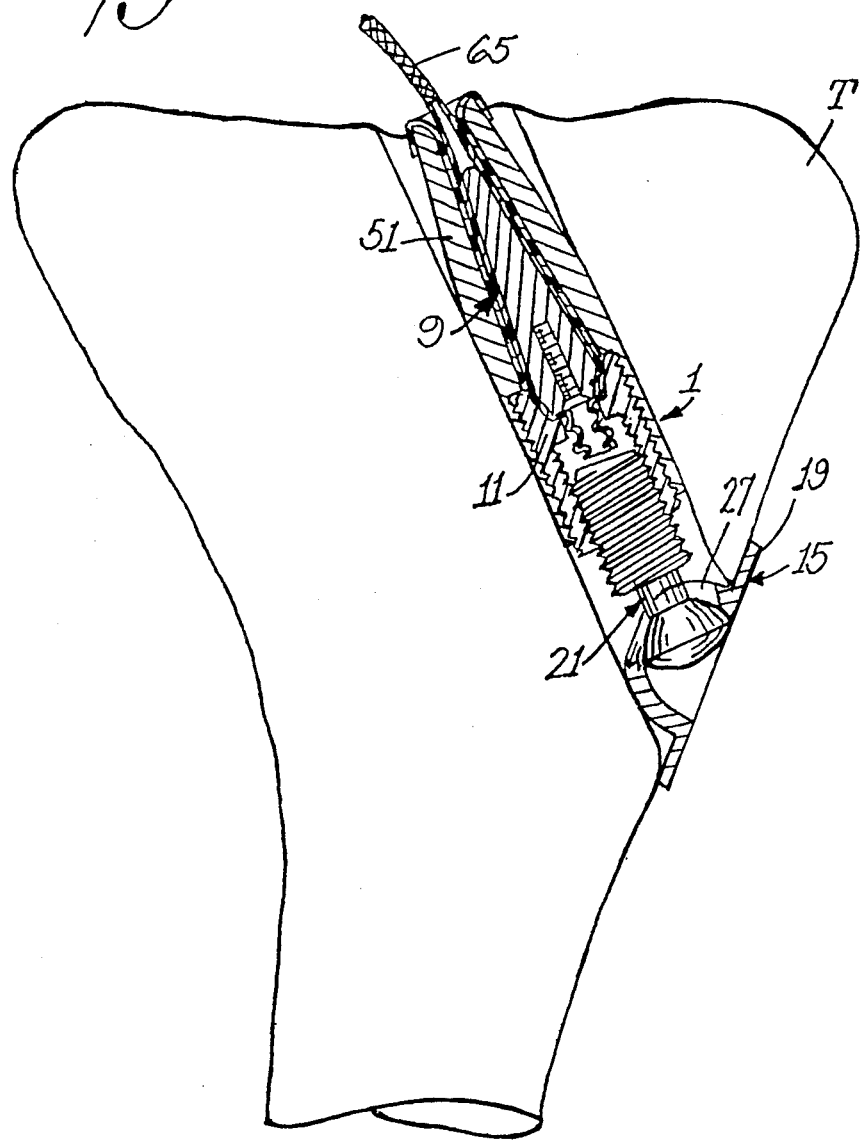

A prosthesis fixation device 1 of the invention is shown in FIGS. 1 and 2. Device 1 comprises a hollow elongated sleeve 3 adapted to fit within a through drill hole in the bone of a patient and having a front end 5, a rear end 7 and an outer wall 8, a wedge 9 capable of being inserted through the rear end 7 of sleeve 3, a ferrule or locking nut 11 provided with an axial through bore 13 internally threaded over a portion of its length, a washer 15 having a cup portion 17 surrounded by a flange portion 19 adapted to lie against the cortical bone of the patient, and a bolt 21 having a head 23 adapted to engage the cup portion 17 of washer 15 and a shank 25 externally threaded over a portion of its length. The convex underside of bolt head 23 is substantially complementary with the concave inner wall of cup portion 17. Bolt shank 25 is adapted to be screwed into the internally threaded portion of bore 13 of locking nut 11. The length of fixation device 1, i.e. the distance between flange portion 19 and front sleeve end 5 when cup portion 17 is engaged with head 23, can thus be universally adjusted to accommodate the anatomy of a particular patient by varying the extent to which bolt 21 is screwed into locking nut 11. In an alternative embodiment not shown in the figures, this universal length adjustment feature may be realized by providing a bolt (such as bolt 21) that is adapted to be screwed into an internally threaded portion of the hollow elongated sleeve adjacent the rear end of the sleeve. In another alternative embodiment not shown in the figures, bolt 21 may be cannulated to permit the administration of e.g. antibiotics into the vicinity of sleeve 3 and wedge 9 of the implanted fixation device. In the fixation device 1 shown in FIGS. 1 and 2, an arcuate slot 27 is provided in cup portion 17 of washer 15 in communication with a central hole 29 to permit the variable angulation of bolt 21 with respect to flange portion 19 in a plane perpendicular to portion 19. A plurality of straight longitudinal ridges, e.g. 31, are provided around the outer wall 8 of the elongated sleeve 3 for preventing the rotation of the sleeve within a through drill hole in a patient's bone.

The interaction of the hollow elongated sleeve and wedge is crucial to the function of the present invention. Thus, for example, in the fixation device 1 of FIGS. 1 and 2, the hollow sleeve 3 has an inner wall 33 defining a bore 35, which bore 35 is open at both ends 5 and 7 and includes a tapered bore portion 37. The cross-sectional thickness of tapered bore portion 37 decreases towards front end 5 in one direction, i.e. in the plane of FIG. 11, but is constant in the perpendicular direction, i.e. in the plane of FIG. 1. Wedge 3 is shaped so that it is capable of being inserted through the rear end 7 of sleeve 3 into bore 35 and advanced forwardly into tapered bore portion 37 until coming to a position of abutment with the inner wall 33 of sleeve 3. In this position of abutment (shown in FIG. 9) a pair of opposed faces 39 and 41 on the outer surface of wedge 9 are substantially congruent with the adjacent inclined surfaces 43 and 45, respectively, of the inner sleeve wall 33. As can be seen in FIGS. 1 and 2, wedge 9 preferably has substantially the shape of a duck bill, with faces 39 and 41 being flat and forming the top and bottom surfaces of the duck bill. Most preferably, the flat wedge faces 39 and 41 are oriented relative to one another at an acute angle of from about 10° to about 15°, and the flat inclined sleeve surfaces 43 and 45 are oriented relative to one another at approximately the same acute angle as surfaces 39 and 41. A threaded hole 47 opening to the rear of wedge 9 is preferably included in wedge 9 to aid in the insertion of the wedge into sleeve 3 during the implantation of device 1 (see FIGS. 4 and 8).

The inner wall 33 of sleeve 3 of fixation device 1 is defined in the region of tapered bore portion 37 by a layer 49 of a strong and resilient polymeric material such as the polyester/polyether block copolymer Hytrel (E. I. du Pont de Nemours & Co.; Wilmington, Del.). Polymeric layer 49 may, for example, be integrally molded or bonded onto the body portion 51 of sleeve 3, or alternatively may be an extruded polymeric piece fitted into the interior of portion 51. The surfaces 39 and 41 of wedge 9 are preferably formed by a strong and resilient polymeric material such as an ultra high molecular weight polyethylene. Thus, wedge 9 may be a polymeric part of one-piece polymeric construction, or alternatively may comprise a polymeric layer molded or bonded onto an interior body portion. By forming surfaces 39, 41, 43 and 45 of such strong and resilient polymeric materials, any damage to the prosthesis caused by the compression of the prosthesis between these surfaces is prevented. Abrasive wear between fixation device 1 and a prosthesis held between sleeve 3 and wedge 9 in use is substantially eliminated by the configuration of the front end portion of sleeve 3 shown in FIG. 11, in which each of flat surfaces 43 and 45 terminates short of front sleeve end 5, and the inner sleeve wall portions 53 and 55 connecting surfaces 43 and 45 with the substantially rectangular bore opening 57 at front end 5 are smoothly and gradually convexly-rounded with gradually increasing separation towards opening 57. This configuration avoids contact of the affixed prosthesis with sharp sleeve or bone drill hole edges in the vicinity of the front end 5 of sleeve 3. The aforementioned polymeric construction of surfaces 39, 41, 43 and 45 also reduces any abrasive wear between the affixed prosthesis and device 1.

The congruent shapes of wedge 9 and sleeve 3 may be different from those shown in the figures herein. For example, the wedge 9 and bore portion 37 may be tapered in the plane of FIG. 1 instead of, or in addition to, the plane of FIG. 2. The congruent surfaces, e.g. 39, 41, 43 and 45, need not be flat and thus in one concept of the invention the congruent wedge and tapered bore portion are both conical, with diametrically opposed surfaces on the conical wedge functioning in the same manner as the opposed flat surfaces 39 and 41 of the duck bill-shaped wedge 9. In the broadest concept of the invention, all that is required is that a cross-sectional dimension of the congruent wedge and sleeve bore be reduced at one location from what that dimension is at a further distance from the front end of the hollow sleeve so that a portion of a prosthesis can be trapped between the sleeve and wedge. Therefore it would be sufficient to practice the broad concept of the invention to provide one or more congruent steps to reduced thickness towards the front sleeve end in an otherwise non-tapered (e.g. cylindrical or rectangular prismatic) wedge and sleeve bore. Tapered wedges and sleeve bore portions such as are shown in the figures herein are, however, highly preferred.

In fixation device 1 a relatively short frustoconical male portion 59 is formed adjacent the rear end of the wedge 9 and a complementary frustoconical female portion 61 is formed at the front end of the locking nut 11. Locking nut 11 is externally threaded along a major portion of its length and is adapted to be screwed in use into an internally threaded portion 63 of sleeve 3 (to the rear of tapered bore portion 37) until portions 59 and 61 become engaged and the locking nut 11 firmly presses the wedge 9 forwardly against the inner wall of the sleeve 3 in the position of abutment shown in FIG. 9. In this situation the sleeve 3, wedge 9 and locking nut 11 are locked together in a rigid assembly. Alternative sleeve/wedge locking elements other than the externally threaded locking nut 11 may be utilized in the present invention. Thus, for example, such a locking element could be of the type found in conventional Luer-type fittings, with the locking element being adapted to be slid foward in a non-threaded rear portion of the hollow sleeve bore and then releasably locked in its desired position by axial rotation within said sleeve bore (i.e. by means of a conventional "twist lock").

Sleeve body portion 51, locking nut 11, washer 15, bolt 21 and the body portion of wedge 9 (when the wedge is not made in a one-piece polymeric construction) are preferably made of a surgical implant metal or metal alloy such as titanium metal, stainless steel or cobalt-chromium-molybdenum alloy. The strong but light weight Titanium-6 Aluminum-4 Vanadium alloy is particularly preferred. These metal or metal alloy parts can be readily manufactured by conventional casting, machining, etc. processes known to those skilled in the art.

The use of fixation device 1 will be described with reference to the implantation of a hollow tubular thin-walled ACL prosthesis 65 of the type disclosed in the aforementioned U.S. patent application Ser. No. 481,612. It is to be understood that a fixation device of the present invention can be used with similar techniques to affix other types of prostheses for the ACL or other ligaments or tendons, or to affix the same type of prosthesis when used to repair or replace other ligaments or tendons than the ACL. The first step in the procedure is to create two substantially cylindrical through drill holes (note broken lines in FIG. 6) in the femur F and tibia T, insert the hollow elongated sleeve 3 through the rear end of the tibial drill hole (at the right of the hole in FIG. 6) and advance the sleeve therein until front sleeve end 5 extends slightly beyond the front end of the tibial drill hole (at the left in FIG. 6), and then thread prosthesis 65 sequentially through the femoral drill hole and hollow sleeve 3 in the direction shown in FIG. 6 using, for example, a leader and thread assembly 67. A device 69 to prevent the trailing end of the prosthesis 65 from being pulled through the femoral drill hole is preassembled with prosthesis 65 prior to this threading step; device 69 may be (but need not necessarily be) a preassembled fixation device 1.

The next step (see FIG. 7) is to pretension the prosthesis 65 to a desired extent, for example with a conventional pretensioning tool 71 or by hand with the use of an appropriate gauge. Note that the length of prosthesis 65 extending beyond the moving gripping portion 73 of tool 71 is cut off before pretension is applied. With prosthesis 65 held in the desired state of pretension by tool 71 (note that the main body of tool 71 is not shown in FIG. 8), wedge 9 is then inserted through the rear end of prosthesis 65 by means of an insertion rod 75 screwed into hole 47 and then advanced forwardly until it reaches its position of abutment against surfaces 43 and 45 of sleeve 3, in which position a portion of prosthesis 65 is firmly held between surfaces 43 and 45 of sleeve 3 and faces 39 and 41 of wedge 9. The pretensioning tool 71 is then released. At this point insertion rod 75 can be removed, although it can also be left in place while locking nut 11 is screwed into place. In either case, the next step is to slip the locking nut 11 over the end of prosthesis 65 and screw the locking nut 11 into the internally threaded portion 63 of sleeve 3 using an insertion tool (not shown) which grips a smooth rear cylindrical portion 77 and diametrical slot 79 on locking nut 11. Locking nut 11 is advanced until it firmly presses the wedge 9 forwardly against the inner wall 33 of sleeve 3, thereby locking the sleeve 3, wedge 9 and locking nut 11 together in a rigid assembly with a portion of prosthesis 65 securely gripped between the hollow sleeve and wedge. Another portion of the prosthesis is held between wedge portion 59 and mating locking nut portion 61.

It remains to install the bolt 21 and washer 15 so that the fixation device cannot be pulled forwardly in the tibial drill hole by the pretensioned prosthesis 65. The end of prosthesis 65 extending beyond the rear end of the locking nut 11 is first cut off, and the bolt 21 is then screwed into the internally threaded axial bore 13 of locking nut 11 while also extending through cup portion 17 of washer 15. To facilitate screwing bolt 21 is provided with a conventional Allen-type slot 81, with a hexagonal cross-section, in head 23. The advancement of bolt 21 into locking nut 11 is continued until the flange portion 19 of washer 15 is pulled firmly against the cortical bone wall adjacent the rear end of the tibial drill hole. It can be seen that the implanted length of the fixation device 1, i.e. the distance between flange portion 19 and front sleeve end 5, is automatically adjusted to its proper value during the installation of bolt 21 and washer 15, as is the implanted angular orientation between flange portion 19 and bolt shank 25 (which can be accommodated within the slot 27). If desired, one or more spikes (not shown in the figures) may be provided on the underside of flange portion 19 to afford a cortical bone-gripping function.

The fully implanted ACL prosthesis 65 and fixation device 1 are shown in FIGS. 9 and 10. It is important to note that bolt 21 and locking nut 11 can be readily unscrewed to release their respective holding (against pulling by prosthesis 65) and locking actions. Thus, if necessary, prosthesis 65 can be readily replaced, readjusted or retensioned with the use of minor surgery in combination with arthroscopic techniques.

I claim:

1. A device for the fixation of a pretensioned ligament or tendon prosthesis to a bone of a patient comprising:
   a hollow elongated sleeve adapted to fit within a through drill hole in said bone and having a front end, a rear end, an inner wall defining a bore and an outer wall, with said bore being open at both the front and rear ends of the sleeve and tapered over a portion of its length with decreasing cross-sectional bore thickness, in at least one dimension, towards said front end;
   a wedge capable of being inserted through the rear end of the sleeve and advanced forwardly into said tapered portion of the bore until coming to a position of abutment with said inner wall of the sleeve, with a pair of opposed faces on the outer surface of said wedge being, when the wedge is in said position of abutment, disposed within said tapered bore portion and substantially congruent with the adjacent surfaces of said inner wall;
   means for locking the sleeve and the wedge together in a rigid assembly with the wedge in said position of abutment; and
   means for holding said rigid assembly to said bone in such a manner that said assembly cannot be pulled forwardly through said drill hole in the patient's bone.

2. A device of claim 1 wherein both said locking means and said holding means are releasable.

3. A device of claim 2 wherein a portion of the sleeve to the rear of said tapered bore portion is internally threaded and said locking means comprises an externally threaded locking nut adapted to be screwed into said internally threaded sleeve portion until it firmly presses the wedge forwardly against the inner wall of the sleeve in said position of abutment.

4. A device of claim 1 wherein said holding means comprises a washer adapted to lie against the cortical bone adjacent the rear end of said drill hole.

5. A device of claim 4 comprising means to adjust the distance between said washer and the front end of the sleeve.

6. A device of claim 2 wherein said holding means comprises a washer adapted to lie against the cortical bone adjacent the rear end of said drill hole.

7. A device of claim 6 comprising means to adjust the distance between said washer and the front end of the sleeve.

8. A device of claim 3 wherein said locking nut is provided with an axial through bore, said axial bore is threaded over a portion of its length and said holding means comprises a washer adapted to lie against the cortical bone adjacent the rear end of said drill hole and a bolt having a head adapted to engage the washer and a shank externally threaded over at least a portion of its length, with said shank adapted to be screwed into the axial bore of said locking nut.

9. A device of claim 8 wherein an angular adjustment of the screw and washer relative to one another is permitted.

10. A device of claim 8 wherein the wedge is provided with a threaded hole open at the rear end of the wedge for the releasable securement of an elongated rod to the wedge.

11. A device of claim 1 wherein said locking means comprises a locking element capable of being inserted through the rear end of the sleeve and advanced forwardly within the sleeve until it firmly presses the wedge forwardly against the inner wall of the sleeve in said position of abutment, and then locked with the sleeve and the wedge to form a rigid assembly of sleeve, wedge and locking element.

12. A device of claim 1 wherein the outer wall of said sleeve is provided with means to prevent the rotation of the sleeve within said drill hole.

13. A device of claim 1 wherein said wedge has substantially the shape of a duck bill, with said pair of opposed faces on the outer surface of the wedge being the top and bottom surfaces of the duck bill-shaped wedge.

14. A device of claim 13 wherein said top and bottom surfaces are substantially flat and oriented relative to one another at an acute angle of from about 10° to about 15°, and said adjacent surfaces of the inner wall are a pair of substantially flat opposed inclined surfaces thereof oriented relative to one another at approximately the same acute angle.

15. A device of claim 14 wherein each of said inclined inner wall surfaces terminates at its front edge short of the front end of the sleeve, with the sleeve opening at said front end being substantially rectangular and the inner wall portion connecting each of said front edges with said front end being smoothly and gradually convexly-rounded with gradually increasing separation between said two connecting inner wall portions.

16. A device of claim 1 wherein said opposed faces on the outer surface of the wedge and said adjacent surfaces of the inner sleeve wall are each formed by a strong and resilient polymeric material.

17. A device for the fixation of a pretensioned ligament or tendon prosthesis to a bone of a patient comprising:
   a hollow elongated sleeve adapted to fit within a through drill hole in said bone and having a front end, a rear end, an inner wall defining a bore and an outer wall, with said bore being open at both the front and rear ends of the sleeve and including a first bore portion of reduced cross-sectional bore thickness, in at least one dimension, with respect to a second bore portion located at a greater distance than said first bore portion from said front end of the hollow sleeve;
   a wedge capable of being inserted through the rear end of the sleeve and advanced forwardly into said bore until coming to a position of abutment with said inner wall of the sleeve, with a face on the outer surface of said wedge being, when the wedge is in said position of abutment, substantially congruent with a surface of said first bore portion;
   means for locking the sleeve and the wedge together in a rigid assembly with the wedge in said position of abutment; and
   means for holding said rigid assembly to said bone in such a manner that said assembly cannot be pulled forwardly through said drill hole in the patient's bone.

18. A method for the fixation of a pretensioned ligament or tendon prosthesis to a bone of a patient comprising the steps of:
   (a) providing a hollow tubular thin-walled ligament prosthesis;
   (b) providing a device of claim 1;
   (c) forming a through drill hole having a front end and a rear end in said bone;
   (d) inserting said sleeve through the rear end of said drill hole and advancing the sleeve therein until the front end of the sleeve is proximate to the front end of the drill hole;

(e) threading one end of said prosthesis through the front end of said sleeve;

(f) placing the prosthesis in a desired state of pretension;

(g) inserting said wedge through said one end of the prosthesis and advancing said wedge forwardly within said prosthesis until it reaches said position of abutment with a portion of said thin-walled prosthesis held firmly between said wedge and said sleeve inner wall;

(h) locking the sleeve and the wedge together in a rigid assembly with the wedge in said position of abutment; and (i) activating said holding means.

* * * * *